United States Patent
Okoshi et al.

(10) Patent No.: US 7,619,109 B2
(45) Date of Patent: Nov. 17, 2009

(54) POLYISOCYANIDE DERIVATIVE HAVING CONTROLLED HELICAL MAIN CHAIN STRUCTURE

(75) Inventors: Kento Okoshi, Aichi (JP); Eiji Yashima, Aichi (JP); Hisanari Onouchi, Aichi (JP); Shin-Ichiro Sakurai, Aichi (JP); Takashi Kajitani, Aichi (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 12/085,696

(22) PCT Filed: Dec. 1, 2006

(86) PCT No.: PCT/JP2006/324115

§ 371 (c)(1),
(2), (4) Date: May 28, 2008

(87) PCT Pub. No.: WO2007/063994

PCT Pub. Date: Jun. 7, 2007

(65) Prior Publication Data

US 2009/0030227 A1    Jan. 29, 2009

(30) Foreign Application Priority Data

Dec. 1, 2005 (JP) ............................. 2005-347943
Sep. 4, 2006 (JP) ............................. 2006-238533

(51) Int. Cl.
*C07C 229/00* (2006.01)
(52) U.S. Cl. ...................................................... 560/35
(58) Field of Classification Search ....................... None
See application file for complete search history.

(56) References Cited

FOREIGN PATENT DOCUMENTS

| JP | 2001-192450 | 7/2001 |
|----|-------------|--------|
| JP | 2004-018762 | 1/2004 |
| JP | 2005-080500 | 3/2005 |

OTHER PUBLICATIONS

Takei et al., Journal of Organometallic Chemistry, 559:91-96 (1998).

*Primary Examiner*—Paul A Zucker
(74) *Attorney, Agent, or Firm*—Peter F. Corless; Christine C. O'Day; Edwards Angell Palmer & Dodge LLP

(57) ABSTRACT

Disclosed are: a method for production of a polyisocyanide derivative having a stable helical main chain structure with a right-handed or left-handed helix or a mixture thereof from a single type of monomer by polymerizing an aromatic isocyanate having a substituent harboring a structure —CONH in the aromatic ring and a hydrophobic moiety having 6 or more carbon atoms in a polymerization solvent, wherein the direction of the helix depends on the polarity of the polymerization solvent; a poly(aromatic isocyanide) derivative produced by the method; and an aromatic isocyanide which is useful as a monomer for use in the production of the poly(aromatic isocyanide) derivative.

4 Claims, 6 Drawing Sheets

[FIG 1]
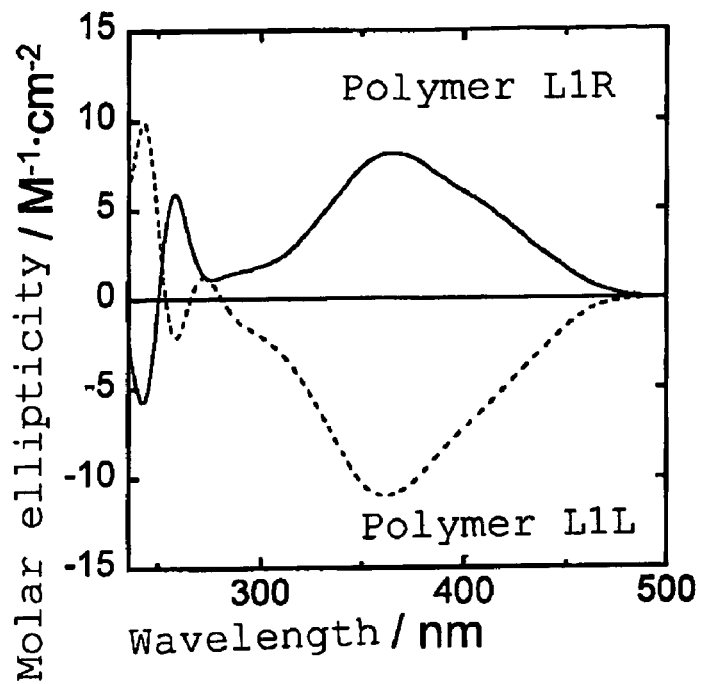
[FIG 2]
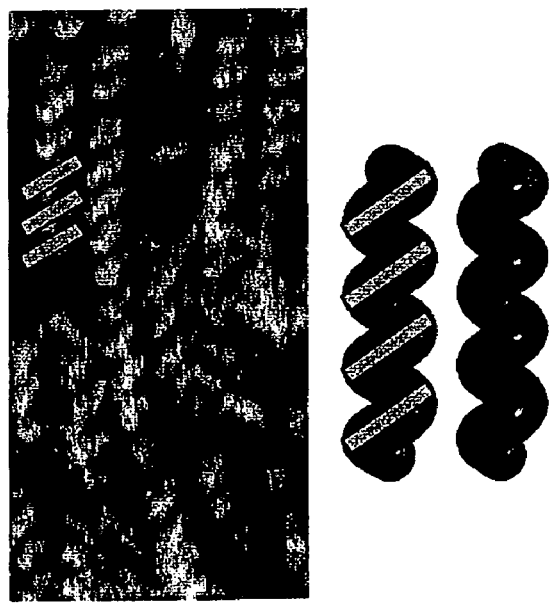
10 x 20 nm

[FIG 3]
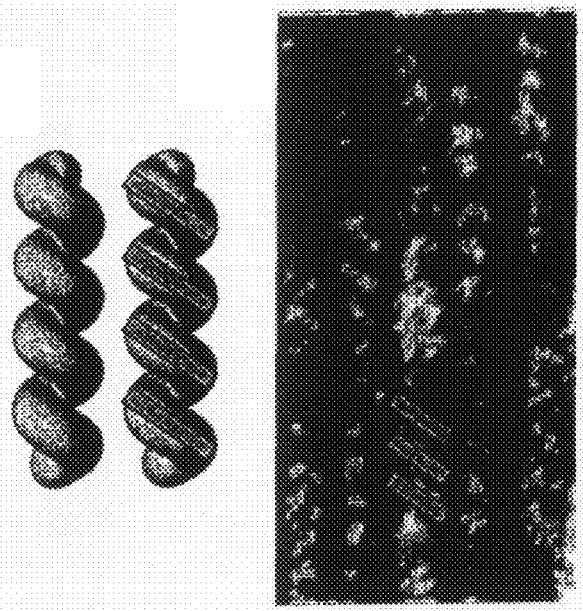
10 × 20 nm
[FIG 4]
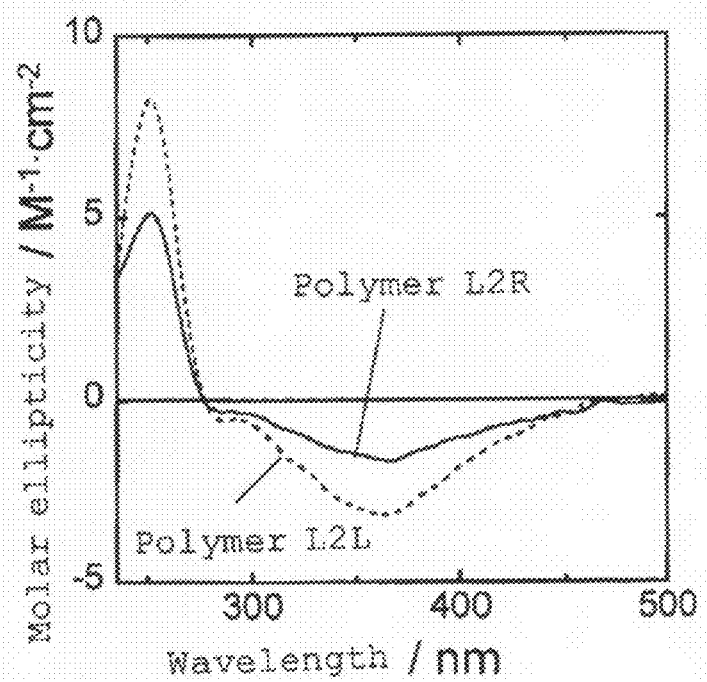

[FIG 5]
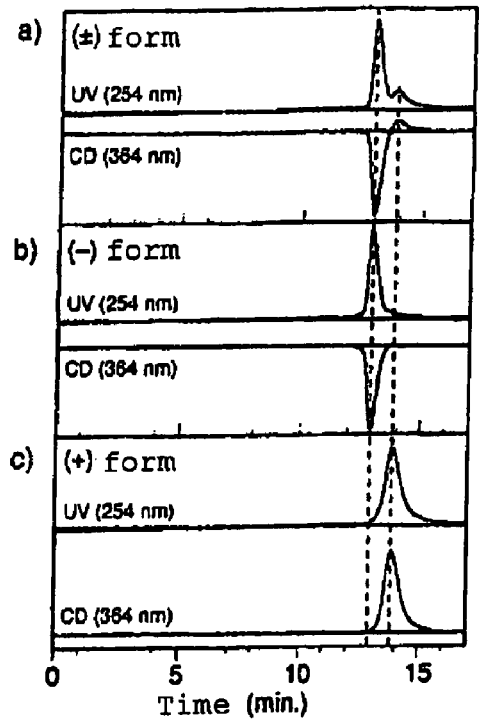
[FIG 6]
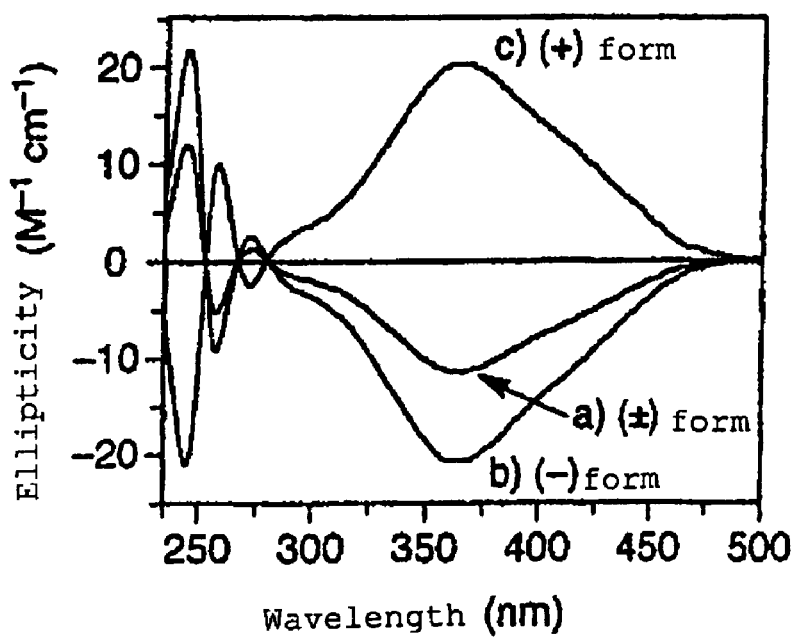

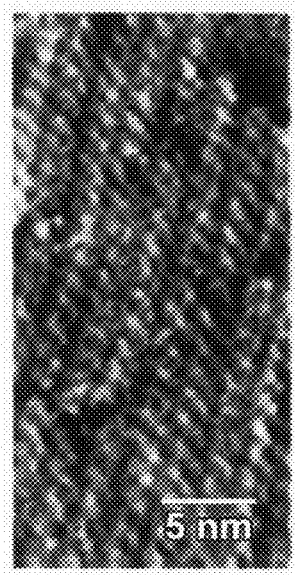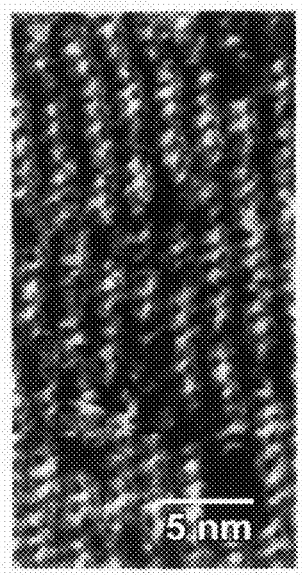
FIG. 7
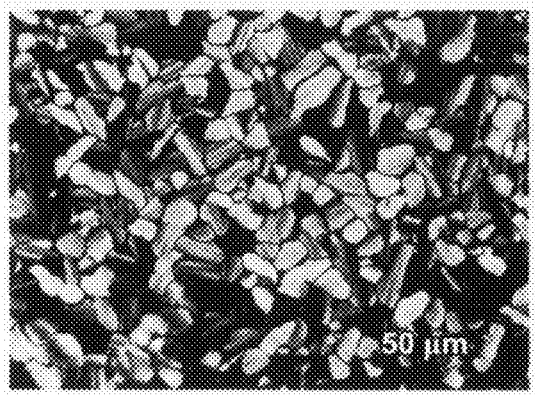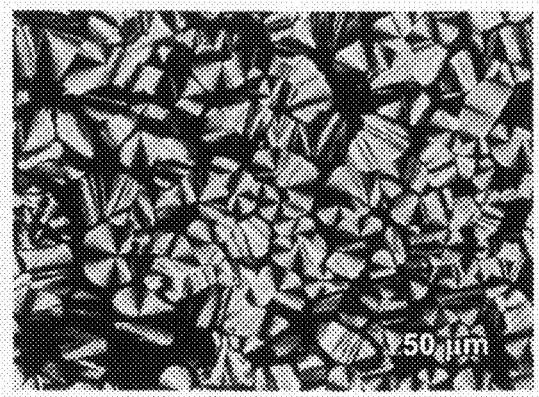
FIG. 8 a) (+) form
b) (−) form
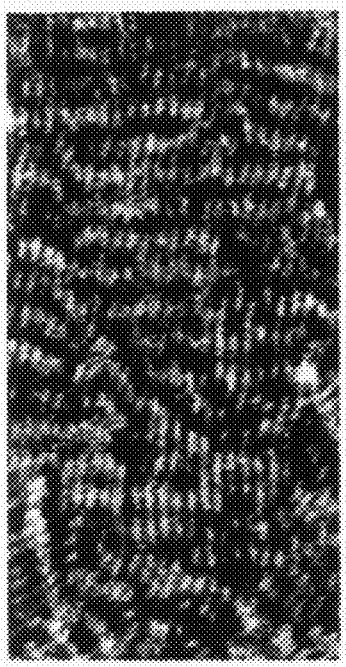
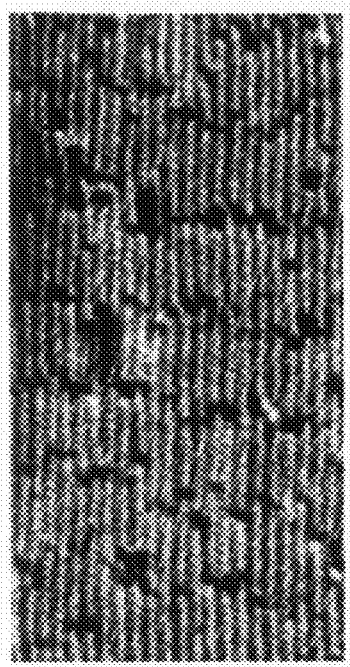
50 × 100 nm
50 × 100 nm
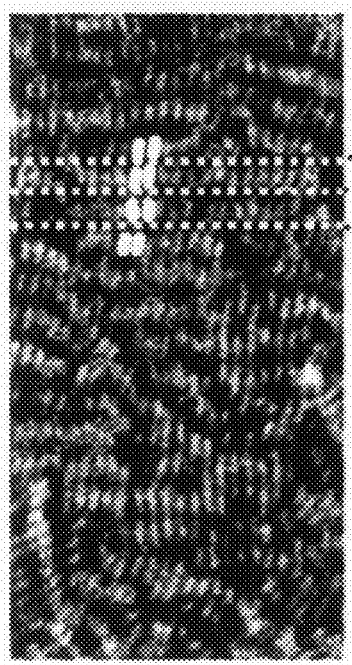
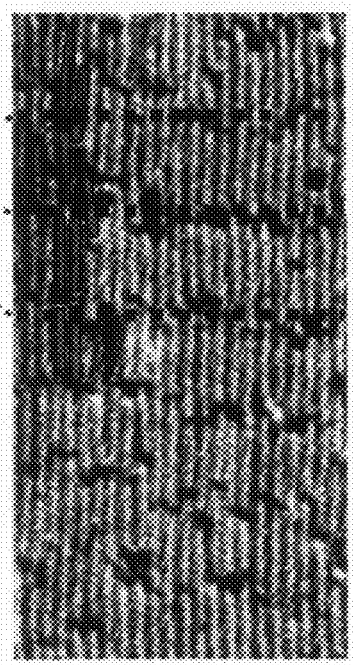
▯ = Polymer Chain
••••• = Lamellar structure in smectic phase
FIG. 9

[FIG 10]
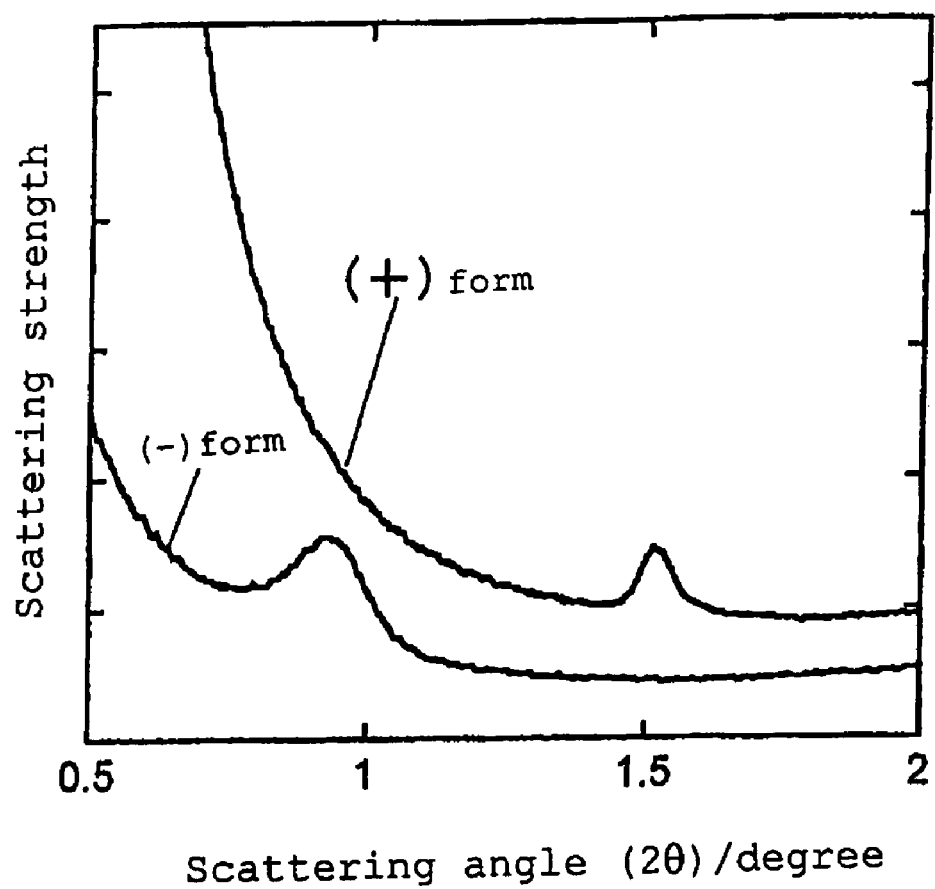

POLYISOCYANIDE DERIVATIVE HAVING CONTROLLED HELICAL MAIN CHAIN STRUCTURE

TECHNICAL FIELD

The present invention relates to, in regard of polyisocyanide derivative that is a static and stable helical polymer, a method for production of a polymer having a main chain structure of which helical structure can be reversed depending on a polymerization reaction condition such as a polymerization solvent and temperature, etc. from a single type of monomer, and a polymer produced by the method. More specifically, the present invention provides a method for production of a polyisocyanide derivative having a stable helical main chain structure with a right-handed or left-handed helix or a mixture thereof from a single type of monomer by polymerizing an aromatic isocyanide having a substituent harboring a structure —CONH in the aromatic ring and a hydrophobic moiety having 6 or more carbon atoms in a polymerization solvent, wherein the handedness of the helix depends on the polarity of the polymerization solvent, a polyaromatic isocyanide derivative produced by the method, and an aromatic isocyanide derivative which is useful as a monomer for the production of the polyaromatic isocyanide derivative.

BACKGROUND ART

Chirality in a helical structure originates from a unique conformation of a polymeric material. DNA and protein, which are the most common helical polymeric material, form a double helix, or a special helix, so-called α-helix, respectively. Both of them consist of only a single enantiomeric isomer having one rotational direction and have a stable right-handed structure. On the other hand, in order to have a left-handed structure, an enantiomeric isomer having opposite rotational direction, that is hardly found in the nature, should be employed as a structural unit.

Recently, artificially synthesized helical polymers have become well known. However, a stable helical polymer predominantly having one handedness often cannot be easily prepared by an asymmetric synthesis. Conventionally, a polymer having a single-handed helical structure should be prepared by using an optically active compound with corresponding handedness as an asymmetric center in the polymer structure (see, Patent Document 1). Thus, in order to obtain a helical structure with opposite handedness, other optically active compound having opposite handedness should be used as a reaction material.

Meanwhile, for a group of polymer which is called dynamic helical polymer, reversion between right-handedness and left-handedness occurs very fast in a solvent. Thus, by introducing a very small number of optically active sites to a side chain of the polymer, the handedness of the entire polymer molecule can be changed to a single one (see, Non-Patent Document 1). In this case, although around room temperature it is possible to observe a polymer having either right-handedness or left-handedness (see, Patent Document 2), since handedness of such polymer group can be easily reversed by temperature, a solvent and an optically active additive, etc. and the helix is dynamic by itself, the handedness of the polymer can be re-reversed depending on outer environments. Thus, practical use of such polymer as a functional material is very limited.

As explained above, producing a polymer having a stable single-handed helical structure, i.e., either right-handed or left-handed, from a single type of monomer remained as an impossible task to achieve until now.

A helical polymer with a static and stable single-handedness can be used as a filler for optical resolution column chromatography, a catalyst for asymmetric synthesis, and an optically active ligand material, etc. Thus, preparing right-handedness and left-handedness simply at low cost is very important to improve resolution efficiency and to obtain a desired optically active compound in asymmetric synthesis.

In addition, since in most cases a helical polymer has a very rigid main chain structure, it shows a cholesteric liquid crystal phase in a solvent or in a molten state (see, Patent Document 3). Inventors of the present invention also have developed a polymer with a very rigid main chain structure or use thereof as a liquid crystal (see, Patent Document 4 and 5).

As such, should the ratio between right-handedness and left-handedness be easily controlled in a main chain helix of a polymer, it becomes also possible to control a helical pitch (period of a helical structure) of a cholesteric liquid crystal phase. By immobilizing such structure as a film, an application to various optical devices can be also achieved simply at low cost.

As other examples of polymer having a rigid rod-like structure described above, lots of polyglutamic acid having a long n-alkyl chain, for instance n-decyl group, have been reported (see, Non-Patent Document 2, 3, 4 and 5). In this regard, it has been also reported that from polyglutamic acid having an alkyl chain longer than n-decyl group not only a characteristic of cholesteric liquid crystal but also hexagonal columnar and smectic phases are observed.

In addition, similar to the polyglutamic acid, some other rigid or semi-rigid polymers such as cellulose, polyisocyanate, polysilane and wholly aromatic polymers have been reported to have thermotropic liquid crystallinity or lyotropic liquid crystallinity.

Patent Document 1: JP-A 56-106907
Patent Document 2: JP-A 2001-294625
Patent Document 3: JP-A 2001-164251
Patent Document 4: WO 01/79310
Patent Document 5: WO 2005/080500
Non-Patent Document 1: E. Yashima, Modern Chemistry, 52 (2000)
Non-Patent Document 2: J. Watanabe, Y. Fukuda, R. Gehani and I. Uematsu, Macromolecules, 17, 1004 (1984)
Non-Patent Document 3: J. Watanabe, H. Ono, A. Abe and I. Uematsu, Macromolecules, 18, 2141 (1986)
Non-Patent Document 4: J. Watanabe, T. Nagase, H. Itoh, T. Ishii and T. Satoh, Mol. Cryst. Liq. Cryst., 164, 135 (1988)
Non-Patent Document 5: In "Ordering in Macromolecular Systems" A. Teramoto, M. Kobayashi and T. Norisue, Eds., Springer-Verlag, Berlin, Heidelberg, p 99-108 (1994)

DISCLOSURE OF THE INVENTION

Problem to be Solved by the Invention

The present invention relates to a method for producing a molecule having a stable right-handed or left-handed helical structure from a single type of monomer in a per-selective manner and controlling the proportion between the right-handedness and the left-handedness thereof. The present invention further relates to a polymeric material of which helical structure can be prepared in any handedness.

Means for Solving the Problem

Inventors of the present invention intensively studied whether or not a helical polymer having one handedness and a helical polymer having opposite handedness can be obtained when an amide group is introduced in a monomer structure for preparing polyisocyanide polymers having a stable helical structure to form a hydrogen bond between the amide groups and a polymerization is carried out while adjusting the strength of hydrogen bond by changing a solvent and temperature, and also whether or not the proportion between the right-handedness and the left-handedness can be controlled. Then, the inventors found that the helical structure of a polymer obtained by specifying a polymerization condition such as a solvent for polymerization. As a result, the inventors found that, the helical structure of a polymeric material can be controlled by changing a polymerization condition such as a solvent for polymerization, etc., and a polymer compound having either a right-handed helical structure or a left-handed helical structure can be obtained from a single type of monomer.

Furthermore, as a result of intensive study, the inventors of the present invention found that polyisocyanide polymers in which an amide group is introduced to form a hydrogen bond between adjacent side chains of the polymer to give isomers having either right-handedness or left-handedness have a significantly different solubility in a solvent, and further found that a mixture of right-handed isomer and left-handed isomer can be separated based on such difference in solubility. Based on such finding, the present invention was completed.

Namely, the present invention relates to a method for production of a polyisocyanide derivative having a stable helical main chain structure with a right-handed or left-handed helix or a mixture thereof from a single type of monomer by polymerizing an aromatic isocyanide having a substituent harboring a structure —CONH in the aromatic ring and a hydrophobic moiety having 6 or more carbon atoms in a polymerization solvent, wherein the handedness of the helix depends on the polarity of the polymerization solvent.

Further, the present invention relates to a polyaromatic isocyanide derivative having a main chain structure with stable right-handed or left-handed helix consisting of a single type of monomer obtained by living polymerization of an aromatic isonitrile comprising an amide group by which an optically active amino acid or derivative thereof is attached to the aromatic ring, more specifically, polyaromatic isocyanide derivative having a stable helical main chain structure represented by the general formula (1) as follows:

[Chemical Formula 1]

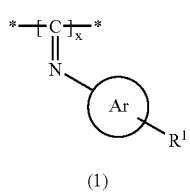

(1)

(wherein, Ar represents an aromatic ring, $R^1$ represents an aminocarbonyl group of an optically active amino acid ester that is esterified with an alkyl group of 6 to 30 carbon atoms or a carbonylamino group of an optically active N-acyl amino acid that is N-acylated with an acyl group having an alkyl group of 6 to 30 carbon atoms and the optically active amino acid is any of levorotatory (S) or dextrorotatory (R) chiral body, and x is a positive number indicating the repeat of polyisocyanide group).

Further, the present invention relates to a method for production of a polyisocyanide polymer having a main chain structure with stable right-handed or left-handed helix consisting of a single type monomer by treating a mixture of polyisocyanide polymer having a main chain structure with right-handed and left-handed helix with an organic solvent to separate the mixture. More specifically, the present invention provides a method for production of a polyisocyanide polymer having a helical main chain structure with a stable right-handed or left-handed helix consisting of a single type of monomer, wherein the method consists of polymerizing an aromatic isonitrile having an amide group in the presence of a catalyst having a characteristic of living polymerization to give a polyisocyanide polymer having a stable helical main chain structure with a right-handed or left-handed helix consisting of a single type of monomer, and treating the mixture of thus-obtained polyisocyanide polymer having a helical main chain structure with a right-handed or left-handed helix consisting of a single type of monomer with an organic solvent to separate them.

The above-stated polyaromatic isocyanide derivatives having a stable helical main chain structure can exhibit a cholesteric liquid crystal phase or a nematic liquid crystal phase in a solvent or in a molten state, thus the present invention provides a liquid crystalline polymer compound which consists of the polyaromatic isocyanide derivative having a stable helical main chain structure as described above.

Further, the present invention relates to an aromatic isocyanide derivative which is represented by the following general formula (3):

[Chemical Formula 2]

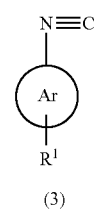

(3)

(wherein, Ar represents an aromatic ring, $R^1$ represents an aminocarbonyl group of an optically active amino acid ester that is esterified with an alkyl group of 6 to 30 carbon atoms or a carbonylamino group of an optically active N-acyl amino acid that is N-acylated with an acyl group having an alkyl group of to 30 carbon atoms, and the optically active amino acid is any of levorotatory (S) or dextrorotatory (R) chiral body). The aromatic isocyanide derivative represented by general formula (3) of the present invention is a compound that can be used as a monomer for producing the polyaromatic isocyanide derivative represented by general formula (1) of the present invention as described above.

The present invention will now be explained in greater detail herein below.

(1) A polyaromatic isocyanide derivative that has a main chain structure with a stable right-handed or left-handed helical structure consisting of a single type of monomer and is produced by living polymerization of an aromatic isonitrile comprising an amide group by which an optically active amino acid or derivative thereof is attached to the aromatic ring.

(2) The polyaromatic isocyanide derivative as described in the above (1), which has a stable helical main chain structure represented by the general formula (1) as follows:

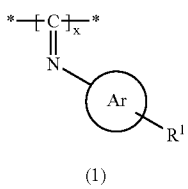

(1)

(wherein, Ar represents an aromatic ring, $R^1$ represents an aminocarbonyl group of an optically active amino acid ester that is esterified with an alkyl group of 6 to 30 carbon atoms or a carbonylamino group of an optically active N-acyl amino acid that is N-acylated with an acyl group having an alkyl group of 6 to 30 carbon atoms, the optically active amino acid is any of levorotatory (S) or dextrorotatory (R) chiral body, and x is a positive number indicating the repeat of polyisocyanide group).

(3) The polyaromatic isocyanide derivative as described in the above (1) or (2), wherein the aromatic ring is a benzene ring.

(4) The polyaromatic isocyanide derivative as described in any one of the above (1) to (3), wherein the optically active amino acid is a natural α-amino acid.

(5) The polyaromatic isocyanide derivative as described in any one of the above (1) to (4), wherein the polyaromatic isocyanide derivative is a polyaromatic isocyanide derivative which can form a hydrogen bond between the adjacent amide groups on a side chain.

(6) The polyaromatic isocyanide derivative as described in any one of the above (1) to (5), wherein the polyaromatic isocyanide derivative has a persistence length of 100 nm or more.

(7) The polyaromatic isocyanide derivative as described in any one of the above (1) to (6), wherein the isomer of the polyaromatic isocyanide derivative having a main chain structure with right-handed or left-handed helix has diastereomeric excess ratio of 90% or more.

(8) The polyaromatic isocyanide derivative as described in any one of the above (1) to (7), characterized in that the molecular weight distribution Mw/Mn, which represents a ratio between weight-average molecular weight Mw and number-average molecular weight Mn, is less than 1.20.

(9) The polyaromatic isocyanide derivative as described in any one of the above (1) to (8), wherein the polyaromatic isocyanide derivative may show a cholesteric liquid crystal phase and/or a nematic liquid crystal phase in a solvent or in a molten state.

(10) The polyaromatic isocyanide derivative as described in any one of the above (1) to (9), wherein the polyaromatic isocyanide derivative forms a smectic liquid crystal phase.

(11) The polyaromatic isocyanide derivative as described in any one of the above (1) to (10), characterized in that it has a membranous shape.

(12) A liquid crystalline composition comprising at least one of the polyaromatic isocyanide derivatives as described in any one of the above (1) to (11).

(13) The liquid crystalline composition as described in the above (12), wherein it forms a smectic liquid crystal phase.

(14) A method for production of a polyaromatic isocyanide derivative having a stable helical main chain structure with either right-handedness or left-handedness, or a mixture thereof comprising one of the isomers in a predominant amount from a single type of monomer by polymerizing an aromatic isocyanide having a substituent harboring a structure —CONH in the aromatic ring and a hydrophobic moiety having 6 or more carbon atoms in a polymerization solvent and in the presence of a polymerization catalyst.

(15) The method as described in the above (14), wherein the polyaromatic isocyanide derivative having a stable helical main chain structure with either right-handedness or left-handedness, or a mixture thereof comprising one of the isomers in a predominant amount from a single type of monomer is produced depending on the polarity of the polymerization solvent.

(16) The method as described in the above (1) or (15), wherein the substituent harboring a structure —CONH in the aromatic ring is an aminocarbonyl group originating from an optically active amino acid ester that is esterified with an alkyl group having 6 to 30 carbon atoms.

(17) The method as described in the above (14) or (15), wherein the substituent harboring a structure —CONH in the aromatic ring is a carbonylamino group originating from an optically active N-acyl amino acid that is N-acylated with a group having an alkyl group of 6 to 30 carbon atoms.

(18) The method as described in any one of the above (14) to (17), wherein the polyaromatic isocyanide derivative having a stable helical main chain structure has either a right-handed or a left-handed helical structure.

(19) The method as described in any one of the above (14) to (18), wherein the polymerization solvent is a non-polar solvent.

(20) The method as described in any one of the above (14) to (19), wherein the polymerization solvent is selected from carbon tetrachloride, diethyl ether, dioxane, dimethyl formamide, benzene, chloroform, dichloromethane, toluene or a mixture thereof.

(21) The method as described in any one of the above (14) to (20), wherein the polymerization solvent is a mixture of a non-polar solvent and a polar solvent.

(22) The method as described in any one of the above (14) to (21), wherein the polar solvent is selected from ethyl acetate, tetrahydrofuran, acetone, methanol, ethanol and a mixture thereof.

(23) A method for production of a polyisocyanide polymer having a main chain structure with stable right-handed or left-handed helix structure consisting of a single type monomer by treating a mixture of polyisocyanide polymer having a main chain structure with right-handed and left-handed helix structure with an organic solvent to separate the mixture.

(24) A method for production of a polyisocyanide polymer having a main chain structure with a stable right-handed or left-handed helix consisting of a single type of monomer, wherein the method consists of polymerizing an aromatic isonitrile having an amide group in the presence of a catalyst having a characteristic of living polymerization for isonitrile to give a polyisocyanide polymer having a main chain structure with a stable right-handed or left-handed helix consisting of a single type of monomer, and treating the mixture of thus-obtained polyisocyanide polymer having a main chain structure with a stable right-handed or left-handed helix with an organic solvent to separate the mixture.

(25) The method as described in the above (23) or (24), wherein the treatment with an organic solvent is based on the solubility difference of the polymer in the organic solvent.

(26) The method as described in the above (14) or (24), wherein the catalyst having a characteristic of living polymerization for isonitrile is an organometallic complex catalyst.

(27) The method as described in the any one of above (14), (24) or (25), wherein the catalyst having a characteristic of living polymerization for isonitrile is binuclear platinum-palladium-μ-ethynediyl complex crosslinked with acetylene that is represented by the following general formula (2):

[Chemical Formula 4]

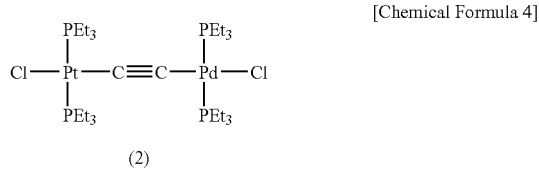

(2)

(28) An aromatic isocyanide derivative which is represented by the following general formula (3):

[Chemical Formula 5]

(3)

(wherein, Ar represents an aromatic ring, $R^1$ represents an aminocarbonyl group of an optically active amino acid ester that is esterified with an alkyl group of 6 to 30 carbon atoms or a carbonylamino group of an optically active N-acyl amino acid that is N-acylated with an acyl group having an alkyl group of 6 to 30 carbon atoms and the optically active amino acid is any of levorotatory (S) or dextrorotatory (R) chiral body).

(29) The aromatic isocyanide derivative as described in the above (28), wherein Ar is a benzene ring.

(30) The aromatic isocyanide derivative as described in the above (28) or (29), wherein the optically active amino acid is a natural α-amino acid.

The present invention is based on the finding that, when an aromatic isocyanide having a substituent harboring a structure —CONH in the aromatic ring is polymerized in a polymerization solvent, a hydrogen bond is formed between adjacent amide groups on the side chain of the polymerized polyaromatic isocyanide derivative, while the formation of such hydrogen bond is affected by a polymerization condition including polarity of the polymerization solvent, etc., and therefore a polyisocyanide derivative having a stable helical main chain structure with either right-handedness or left-handedness, or a mixture thereof comprising one of the isomers present in a predominant amount can be prepared from a single type of monomer in a conventional manner. Thus, according to the method of the present invention, by using the monomer of the present invention and adjusting the polymerization condition for the single type of monomer, it is possible to control the helical structure of the main chain of generated polymer to be any of right-handedness or left-handedness.

The present invention further provides an optically active polyisocyanide polymer which is a homopolyisocyanide polymer produced from the polymerization of a single type of monomer and the structure of the polymer main chain is a helix wherein either left-handed helix (M) or right-handed helix (P) is predominant over the other. The polyisocyanide polymer of the present invention has a static helical structure that can maintain the helical structure very stably against an environmental change such as temperature and a solvent, etc.

The polyisocyanide derivative of the present invention, which is a static and stable helical polymer, is polymerized in the presence of a catalyst which has a characteristic of living polymerization and isomers having a main chain helical structure with stable right-handedness or left-handedness are simultaneously polymerized from a single type of monomer, and by taking advantage of a different solubility in a solvent, isomers having a main chain helical structure with right-handedness or left-handedness can be separated with diastereomeric excess ratio of 90% or more.

Both kinds of the polymer with either right-handed or left-handed helical structure having the same monomer unit as prepared according to the method of the present invention can be used as a filler for optical resolution column chromatography, a catalyst for asymmetric synthesis, and an optically active ligand material, etc.

Furthermore, since the polyisocyanide derivative of the present invention is produced in accordance with a living polymerization process, it has a very narrow molecular weight distribution and also a very rigid main chain structure. Therefore, the polymer chains form a row in a solvent or in a molten state to express a smectic liquid crystal phase in which a lamellar structure is formed.

Such voluntarily formed one-dimensional periodic structure in a scale of several tens of nanometers is a liquid crystal phase of which experimental reproduction has been recently confirmed by using a rod-shaped polymer. The voluntarily formed nanoscale structure can be easily immobilized by evaporating a solvent when it is present in a solution or by cooling to the glass transition temperature thereof or below when it is in a molten state. Thus, by using such structure, molecular elements such as a retardation adjustable phase difference plate, a sensor for recognizing chemicals, a device for high-density recording, and one-dimensional optical crystals, etc. can be produced simply at low cost without any big-sized manufacturing facility.

The polyisocyanide polymer of the present invention is characterized in that it is a homopolymer having an isocyanide (C=N) group. It is further characterized in that it has an amide group as a substituent on the nitrogen atom of the isocyanide group. Due to the presence of the amide group, not only a hydrogen bond can be formed between adjacent side chains so that a stable helical structure can be formed but also solubility in an organic solvent becomes different, enabling an easy separation of the polyisocyanide polymer having a left-handed (M) or a right-handed (P) helical structure based on their different solubility in an organic solvent.

As a substituent on the nitrogen atom of the isocyanide group that is preferred in the present invention, example includes an aromatic group to which an amide group is bonded. The amide group may bind to the aromatic group from either the carbonyl side or the amino side of the amide group. Considering that the amide group is for the formation of a hydrogen bond, any one of the bonding directions is acceptable.

As an aromatic group, example includes, a monocyclic, a polycyclic or a condensed cyclic 6-membered aromatic ring with a carbon atom of 6 to 30, preferably 6 to 20, and more preferably 6 to 10. Preferred aromatic ring includes a benzene ring and a naphthalene ring, etc. With respect to the position of an amide group that is linked to the aromatic group, any one of ortho, meta and para position is acceptable. However, to ensure the formation of sufficient number of hydrogen bonds, a position that is far from the main chain of the polymer is preferred, like a para position.

With respect to the polyisocyanide polymer of the present invention, the preferred isocyanide (C=N) group includes the following Type 1 and Type 2.

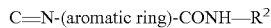  Type 1

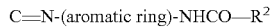  Type 2

(wherein $R^2$ represents a residue of an amide group)

The isocyanide (C=N) group of the present invention can be any one of the above Type 1 or Type 2. For $R^2$ residue of an amide group, any one which can stably form a helical structure, does not impede the formation of hydrogen bond between amide groups, and can cause a different solubility in an organic solvent can be used, and it is not specifically limited. However, in order to stabilize the helical structure, an optically active group is preferred.

With respect to the monomer of the present invention, any aromatic isocyanide having a —CONH group in the aromatic ring to form a hydrogen bond can be used. Aromatic isocyanide as a preferred monomer includes the aromatic isocyanide derivative which is represented by the general formula (3) as described above.

The aromatic isocyanide derivative preferred in the present invention includes the aromatic isocyanide derivative represented by the following general formula (4):

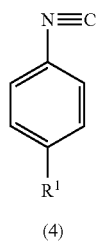

[Chemical Formula 6]

(4)

(wherein, $R^1$ represents an aminocarbonyl group of an optically active amino acid ester that is esterified with an alkyl group of 6 to 30 carbon atoms or a carbonylamino group of an optically active N-acyl amino acid that is N-acylated with an acyl group having an alkyl group of 6 to 30 carbon atoms and the optically active amino acid is any of levorotatory (S) or dextrorotatory (R) chiral body).

The optically active group having a hydrophobic residue includes a group derived from an optically active amino acid ester that is esterified with an alkyl group of 6 to 30 carbon atoms or a group derived from an optically active N-acyl amino acid that is N-acylated with an acyl group having an alkyl group of 6 to 30 carbon atoms, but not limited thereto.

For the "substituent harboring a structure —CONH" which is preferred in the present invention, when $R^1$ of general formula (1) or general formula (3) represents an aminocarbonyl group of an amino acid of which carboxylic group is esterified with an alkyl group of $C_6$-$C_{30}$, preferably $C_6$-$C_{22}$, it corresponds to the above-stated "Type 1." On the other hand, when $R^1$ represents a carbonyl amino group of an amino acid of which amino group is amidated with an alkyl group of $C_6$-$C_{30}$, preferably $C_6$-$C_{22}$, it corresponds to the above-stated "Type 2." If a remaining portion excluding the amino group and the carboxylic group in an amino acid is described as "AA*" and $R^1$ of general formula (1) or general formula (3) represents an aminocarbonyl group of an amino acid of which carboxylic group is esterified with an alkyl group of $C_6$-$C_{30}$, preferably $C_6$-$C_{22}$, $R^1$ is represented by the following general formula (5);

  (5)

Furthermore, if $R^1$ of general formula (1) or general formula (3) represents a carbonylamino group of an amino acid of which amino group is amidated with an alkyl group of $C_6$-$C_{30}$, preferably $C_6$-$C_{22}$, it is represented by the following general formula (6);

  (6)

R and $R^2$ of the above-stated general formula (5) and (6) represent a group to provide hydrophobicity to the residues, and AA represents a remaining portion excluding the amino group and the carboxylic group in an amino acid and is to provide an optical activity to the group.

With respect to the amino acid of the above-stated general formula (5) and (6), it is not specifically limited as long as it is optically active. However, a natural α-amino acid is preferable in terms of easy obtainability. An optically active compound can be either a D form or a L form. Preferred amino acids include alanine, leucine, isoleucine, and threonine, etc.

With respect to the hydrophobic group in R group of the above-stated general formula (5), example includes a linear or branched alkyl group having a carbon atom of at least 6, preferably 6 to 30, 6 to 22, or 6 to 20.

With respect to the hydrophobic group in $R^2$ group of the above-stated general formula (6), example includes a linear or branched alkyl group having a carbon atom of at least 6, preferably 6 to 30, 6 to 22, or 6 to 20 or an alkoxy group which can be derived from the alkyl group.

Examples of the preferred alkyl group include an octyl group, a decyl group and a dodecanyl group, etc.

These monomers can be prepared according to various well-known methods. As an example of the preferred preparation method, nitrobenzene is amidated by using an optically active amino acid ester, reducing the nitro group to an amino group and carrying out a formylation of the amino group by using formic acid or reactive derivatives thereof followed by producing an isonitrile using triphosgene, etc. In addition, by using nitroaniline, it is also possible that acylation into an N-acylated optically active amino acid is first carried out followed by the same reaction processes as described above to prepare the aromatic isocyanide represented by general formula (3) or (4).

These monomers can be polymerized according to a method which is conventionally employed for the preparation of polyisocyanide. For instance, a reaction in the presence of a transition metal catalyst in a polymerization solvent can be mentioned. The transition metal catalyst that can be used includes salts and complexes of nickel or rhodium, etc. Nickel slat is preferred. Preferable example of nickel salt includes nickel chloride and the like.

As an example of a polymerization solvent, there are halogenated hydrocarbons such as carbon tetrachloride, chloroform and dichloromethane; ethers such as diethyl ether, dioxane and tetrahydrofuran; ketones such as acetones; esters such as ethyl acetate; aromatic hydrocarbons such as benzene and toluene and; dialkylamides such as dimethyl formamide, etc. In addition, in order to enhance the polarity of the solvent, it may further comprise a small amount of alcohols such as methanol and ethanol, etc. These solvents can be used alone but also in a form of any mixture.

The polymerization temperature is 0° C. to 200° C., preferably from room temperature to 150° C.

After the completion of the polymerization reaction, the product can be separated by adding alcohols such as methanol and the like to the reaction mixture and then isolating the precipitate therefrom. If necessary, it can be further purified by using various purificational means.

As explained above, the polyaromatic isocyanide derivative having a stable helical main chain structure represented by the above general formula (1) can be obtained. While the helical structure originates from the twisted main chain of the polymer, it appears that by forming a hydrogen bond in certain direction between adjacent amide groups on the side groups of the polyaromatic isocyanide derivative the stability of the helical structure is maintained.

The polyaromatic isocyanide derivative represented by the general formula (1) of the present invention comprises an aromatic ring which is the same as the one for the monomer, and the polyaromatic isocyanide derivative represented by the general formula (1) which is preferred in the present invention includes the polyaromatic isocyanide derivative having the following general formula (7) wherein the aromatic ring is a benzene ring:

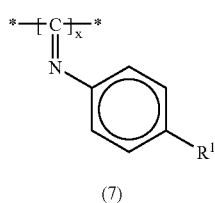

[Chemical Formula 7]

(7)

(wherein, $R^1$ represents an aminocarbonyl group of an optically active amino acid ester that is esterified with an alkyl group of 6 to 30 carbon atoms or a carbonyl amino group of an optically active N-acyl amino acid that is N-acylated with an acyl group of 6 to 30 carbon atoms, the optically active amino acid is any of levorotatory (S) or dextrorotatory (R) chiral body and x is a positive number indicating the repeat of polyisocyanide group). $R^1$ and x in the general formula (7) are the same as those described for the above-described general formula (1)).

The polyaromatic isocyanide derivative represented by the general formula (1) of the present invention can have a molecular weight that is not specifically limited. Preferably, however, it can be 10000 to 1000000, preferably 30000 to 500000, more preferably around 50000 to 500000, or around 50000 to 150000. The repeat number x in the general formula (1) can be around 50 to 2000, preferably around 150 to 1500. In addition, longer persistence length of the polyaromatic isocyanide derivative is preferable. For instance, it can be 5 nm or more, preferably 10 nm or more, more preferably 20 nm or more, or 50 nm or more, preferably 100 nm or more.

The polyaromatic isocyanide derivative of the present invention is a solid crystal phase at room temperature, and it can be subjected to any type of molding with conventional polymeric materials. For instance, it can be molded into a membranous shape, and when molded into such shape it can be converted to be a more functional polymeric material by aligning the polymer direction.

It has been known that the handedness of a helical structure of helical polyisocyanide polymer is as follows: i.e., a positive peak appearing near 300 to 400 nm in CD spectrum, which is a main absorption band region of the main chain of polyisocyanide compound, indicates right-handedness of the main chain helix, while a negative peak appearing near the region indicates left-handedness of the main chain helix (e.g., see Takei, F.; Hayashi, H; Onitsuka, K.; Kobayashi, N.; Takahashi, S. Angew. Chem., Int. Ed. 2001, 40, 4092-4094). Therefore, the handedness of a helical structure can be conveniently determined by a CD spectrum measurement. It can be also further confirmed by directly measuring the surface structure using AFM (Atomic Force Microscopy), etc.

In the conventional methods, the handedness of a helical structure of a polymer is determined by the chirality of a monomer used. However, according to the method of the present invention, it is evident that even for a single type of monomer, i.e., a monomer with same chirality, helical handedness can be decided based on a change in polymerization conditions. This appears to be due to the fact that an aromatic isocyanide comprising an optically active form which has an amide group is used as a monomer. It is believed that such monomer can form a hydrogen bond which helps to maintain a stable helical structure in either handedness, without depending on the chirality of the monomer.

As it is described in the comparative examples below, when a monomer includes an ester bond instead of an amide bond, the helical structure cannot be controlled. From such result, it is believed that the presence of an amide bond plays a key role for controlling the handedness of a helical structure.

Furthermore, when the carbon atom of a hydrophobic moiety in a group which is linked to an amide group is five or less, the resultant helical structure is always left-handed in any kind of solvents and reaction temperatures, making it impossible to control the handedness of a helical structure. Therefore, it is believed that the hydrophobicity of such group also plays a key role for controlling the handedness of a helical structure.

With respect to the polymerization condition, choice of a solvent to be used appears to be important. When carbon tetrachloride, diethyl ether, dioxane, dimethyl formamide, benzene, chloroform, dichloromethane, toluene or a mixture thereof is used as a polymerization solvent during polymerization process, it causes an occurrence of a positive CD peak in the wavelength range of 320 to 400 nm which originates from the main chain of the polymer, resulting in a right-handed helical structure. On the other hand, when a mixture solvent in which a polar solvent such as ethyl acetate, tetrahydrofuran, acetone and ethanol is added to a non-polar solvent such as toluene is used, it causes an occurrence of a negative CD peak in the wavelength range of 320 to 400 nm which originates from the main chain of the polymer, resulting in a left-handed helical structure. The polar solvent can be added in an amount of 1:0.001 to 1, preferably 1:0.005 to 0.1 relative to the non-polar solvent such as toluene and the like, but not limited thereto. In addition, by admixing a polar solvent with a non-polar solvent with a certain mixing ratio, the helical handedness can be arbitrarily controlled.

With respect to the polymerization temperature, it is believed that a left-handed helical structure is more easily formed at a high temperature, for example, 60° C. or above, preferably 80° C. or above.

In this connection, if a right-handed helical structure is desired, it is preferable that the polymerization is carried out at a relatively low temperature such as room temperature using carbon tetrachloride, diethyl ether, dioxane, dimethyl formamide, benzene, chloroform, dichloromethane, toluene or a mixture thereof. On the contrary, if a left-handed helical structure is desired, it is preferable that the polymerization is carried out at a relatively high temperature such as 100° C. using a mixture solvent in which a polar solvent such as ethyl acetate, tetrahydrofuran, acetone and ethanol is added to a non-polar solvent such as toluene. Such effect is especially well observed for the generation of a right-handed helical structure in carbon tetrachloride and a left-handed helical structure in toluene at 100° C. (see the following Examples).

Further, as a method of polymerizing an isonitrile which is required for the production of the polyisocyanide polymer of the present invention, living polymerization can be mentioned. The living polymerization method itself is a publicly well-known method and the polymerization can be carried out in accordance with known operational means. For a catalyst having a characteristic of living polymerization for isonitrile to implement the method of the present invention, various well-known catalysts can be used. Preferably, the catalyst is an organometallic catalyst which comprises a metal such as palladium and platinum. More preferably, it is a binuclear platinum-palladium-m-ethynediyl complex crosslinked with acetylene that is represented by the general formula (2) described before. This complex can be produced according to the method described by Onitsuka, et. al. (K. Onitsuka, K. Yanai, et al., Organometallics 1994, 13, 3862-3867; K. Onitsuka, T. Joh, et al., Bull. Chem. Soc. Jpn. 1992, 65, 1179-1181).

Polymerization is preferably carried out in the presence of a solvent such as tetrahydrofuran (THF). For a solvent, any solvent which can dissolve the monomer of the present invention can be used. Preferably, ethers such as THF can be mentioned. With respect to the concentration of the monomer, it can be between 0.0001 M and 5 M, preferably between 0.001M and 1M. The polymerization temperature can be selected within the range from room temperature to the boiling point of the solvent. Preferably, it can be in the range of 50 to 70° C.

Weight-average molecular weight (Mw) of the polyisocyanide polymer produced according to the method of the present invention can be in the range of 10000 to 1000000, preferably 30000 to 500000, more preferably 50000 to 150000, as stated before. With respect to the molecular weight distribution Mw/Mn, which represents a ratio between weight-average molecular weight Mw and number-average molecular weight Mn, it is not specifically limited. Preferably, it is less than 1.50, more preferably 1.20 or less, or 1.16 or less.

According to the polymerization method described above, both the polyisocyanide polymer having left-handed helical structure (M) and the polyisocyanide polymer having right-handed helical structure (P) are obtained as a mixture. Until now, separation of such mixture was very difficult. However, the polyisocyanide polymer having left-handed helical structure (M) and the polyisocyanide polymer having right-handed helical structure (P) obtained from the present invention, both the polyisocyanide polymer comprising an amide group, are surprisingly found to have a different solubility in an organic solvent. Thus, when the mixture is treated with an organic solvent, a polymer having a helical structure with specific handedness becomes dissolved while the other polymer having a helical structure with opposite handedness becomes precipitated. As a result, by filtering the polymer mixture, a polyisocyanide polymer which has a helical structure predominantly with one specific handedness over the other can be obtained. Although not specifically limited, the diastereomeric excess ratio of one type of isomer is 80% or more, preferably 90% or more. By appropriately selecting an organic solvent, diastereomeric excess ratio of 90% or more can be usually obtained.

The organic solvent may vary depending on the types and the molecular weight of the amino acids comprised in the polyisocyanide polymer. In addition to acetone, a mixture solvent comprising more than one kind of solvents can be used, for example, acetone and chloroform, or acetone and tetrahydrofuran, etc. Acetone is a particularly preferred organic solvent. The amount of an organic solvent varies depending on the types of organic solvent or the polyisocyanide polymer. In general, it is in an amount of 10 to 5000 times, preferably 100 to 1000 times of the weight of the polyisocyanide polymer, but not limited thereto.

As a means of treatment, the mixture of polyisocyanide polymer of the present invention is suspended in an organic solvent, fully stirred at the temperature of from room temperature to the boiling point of the solvent, preferably near room temperature, and the insoluble matters are filtered off to separate them from the solution. The insoluble matters, wherein one type of isomer is present in an excess amount compared to the other, can be used as it is. Alternatively, by re-solubilizing them in chloroform or THF, etc., it can be re-precipitated for purification. Further, by distilling off the organic solvent from the solution obtained after filtering by using a conventional method, a solid phase wherein one type of isomer is present in an excess amount compared to the other can be obtained.

The helical structure of thus-obtained polyisocyanide polymer wherein one type of isomer is present in an excess amount compared to the other can be analyzed according to various well-known methods. For instance, with respect to the polyisocyanide polymer having a helical structure, it is known that a positive peak appearing near 300 to 400 nm in CD spectrum, which is a main absorption band, indicates right-handedness of the main chain helix, while a negative peak appearing near the region indicates left-handedness of the main chain helix (Takei, F.; Hayashi, H; Onitsuka, K.; Kobayashi, N.; Takahashi, S. Angew. Chem., Int. Ed. 2001, 40, 4092-4094).

A liquid crystal display element which uses the liquid crystal composition of the present invention is not specifically limited. Various display types including a helical distortion type, SSFLC type, TSM type, G-H (guest-host) type, field sequential color type can be used. Furthermore, a method of driving a liquid crystal element which uses the liquid crystal composition of the present invention can be a passive driving type including a segment type and a simple matrix type, etc. or an active driving type including TFT (thin-film transistor) type, and MIM (metal-insulator-metal) type, etc.

According to the present invention, a polymeric material having a helical structure with either right-handedness or left-handedness can be produced from a single type of monomer simply at low cost. Thus, a polymeric material having a static and stable helical structure with single handedness, i.e. either right-handedness or left-handedness, can be obtained from a single type of monomer. Producing a polymer having a helical structure with either right-handedness or left-handedness simply at low cost is very important to achieve an improvement in resolution efficiency when the polymer is used as a filler for optical resolution column chromatography, a catalyst for asymmetric synthesis, and an optically active ligand material, etc., and the obtainment of a desired optically active compound via an asymmetric synthesis.

Furthermore, according to the method of the present invention, for obtaining the static and stable polyisocyanide polymer derivative, the polymerization can be carried out by using a catalyst with a characteristic of living polymerization to provide simultaneously the isomers having either a right-handed or left-handed stable main chain helical structure from a single type of monomer, and then each isomer having either a right-handed or left-handed main chain helical structure can be separated in a diastereomeric excess ratio of 90% or more based on their different solubility in a solvent.

Still furthermore, since the polyisocyanide derivative of the present invention has a very rigid main chain structure, in a solvent or in a molten state it shows a cholesteric liquid crystal phase and a nematic liquid crystal phase. By changing a condition for the polymerization reaction and the post-reaction treatment, it is possible to control the ratio between right-handedness and left-handedness of the main chain helix so that a helical pitch (period of a helical structure) of a cholesteric liquid crystal phase produced can be also controlled freely.

The nano-scale structure that is voluntarily formed as explained above can be easily immobilized by evaporating a solvent or by cooling to the glass transition temperature or below. In addition, its use for a filter for circular polarizing plate (infrared ray with a wavelength of 1550 nm and 1300 nm) which is used in an optical communication, a retardation adjustable phase difference plate, a sensor for recognizing chemicals, a device for high-density recording, etc. can be considered. Moreover, it becomes possible to produce such molecular element simply at low cost without any big-sized manufacturing facility.

BRIEF DESCRIPTION OF THE DRAWINGS

FIG. 1 shows a circular dichroism (CD) spectrum of the polymer L1R and the polymer L1L, i.e., poly(4-isocyanobenzoyl-L-alanine decyl ester) polymer having a right-handed helical structure or a left-handed helical structure, respectively, obtained according to the method of the present invention;

FIG. 2 is a photograph showing the observation result obtained from AFM of the polymer L1R, i.e., poly(4-isocyanobenzoyl-L-alanine decyl ester) polymer having a right-handed helical structure of the present invention instead of a drawing. On the left column of FIG. 2, the observation result is shown as a model;

FIG. 3 is a photograph showing the observation result obtained from AFM of the polymer L1L, i.e., poly(4-isocyanobenzoyl-L-alanine decyl ester) polymer having a left-handed helical structure of the present invention instead of a drawing. On the right column of FIG. 3, the observation result is shown as a model;

FIG. 4 shows a CD spectrum of the polymer L2R and the polymer L2L, i.e., poly(4-isocyanobenzoyl-L-lactic acid decyl ester) polymer comprising no amide bond as a comparative example;

FIG. 5 shows the measurement result of SEC elution profile of (±) form, (−) form and (+) form of the polyisocyanide polymer of the present invention by using a UV detector and CD detector.

FIG. 6 shows a CD spectrum of (±) form, (−) form and (+) form of the polyisocyanide polymer of the present invention;

FIG. 7 is an AFM photograph taken for (±) form, (−) form and (+) form of the polyisocyanide polymer of the present invention instead of a drawing;

FIG. 8 is a polarizing microscopic photograph taken for the chloroform solution of (−) form and (+) form of the polyisocyanide polymer of the present invention instead of a drawing;

FIG. 9 is an AFM photograph taken for (−) form and (+) form of the polyisocyanide polymer of the present invention instead of a drawing; and FIG. 10 shows a result obtained from the measurement of narrow angle X-ray scattering profile of a solid sample which was prepared from the concentrated chloroform solution of (−) form and (+) form of the polyisocyanide polymer of the present invention by slowly evaporating the solvent.

BEST MODE FOR CARRYING OUT THE INVENTION

The present invention is illustrated in more detail by the following examples, but should not be construed to be limited thereto.

Meanwhile, nuclear magnetic resonance (NMR) spectrum was measured by using Varian AS500 spectrometer under the operation condition of 500 MHz for $^1$H-NMR and 125 MHz for $^{13}$C-NMR having tetramethylsilane (TMS) as an internal standard.

Infra-red (IR) absorption spectrum was measured by using Jasco FT/IR-680 spectrophotometer.

Absorption spectrum and ellipsoidal (CD) spectrum were measured by using Jasco V570 spectrophotometer and Jasco J820 spectropolarimeter, respectively, with a quartz cell having an optical path length of 1.0 mm, wherein the concentration of the polymer was calculated based on a monomer unit.

Rotatory power was measured by using Jasco P-1030 polarizer with a quartz cell having an optical path length of 2.0 cm.

Size exclusion chromatography (SEC) was performed by using Jasco PU-2080 which is equipped with a UV-Vis detector (Jasco UV-2070) and a CD detector (Jasco CD-2095). In addition, two SEC columns (Tosoh TSKgel Multipore HXL-M SEC column; 30 cm) were connected to the system and THF solution comprising tetra-n-butyl ammonium bromide (0.1 wt %) was used as an eluent with a flow rate of 1.0 mL/min. Molecular weight calibration curve was obtained by using a polystyrene standard material.

Atomic force microscopy (AFM) was carried out by using the microscope of Veeco Instruments Nanoscope IIIa or Nanoscope IV on the basis of highly oriented pyrolytic graphite (HOPG). Dry benzene solution of each polymer was prepared (0.015 mg/mL) and 20 mL of the solution was cast on HOPG to obtain a sample. Solution casting was carried out at room temperature under the atmosphere of benzene vapor. After the exposure to the benzene vapor for additional twelve hours, it was dried under reduced pressure.

EXAMPLES

Example 1

Preparation of 4-isocyanobenzoyl-L-alanine Decyl Ester

4-Isocyanobenzoyl-L-alanine decyl ester monomer was prepared according to the following preparation scheme:

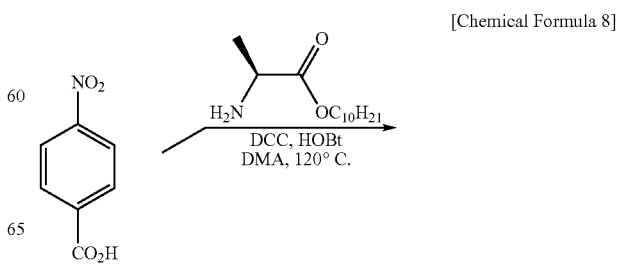

[Chemical Formula 8]

-continued

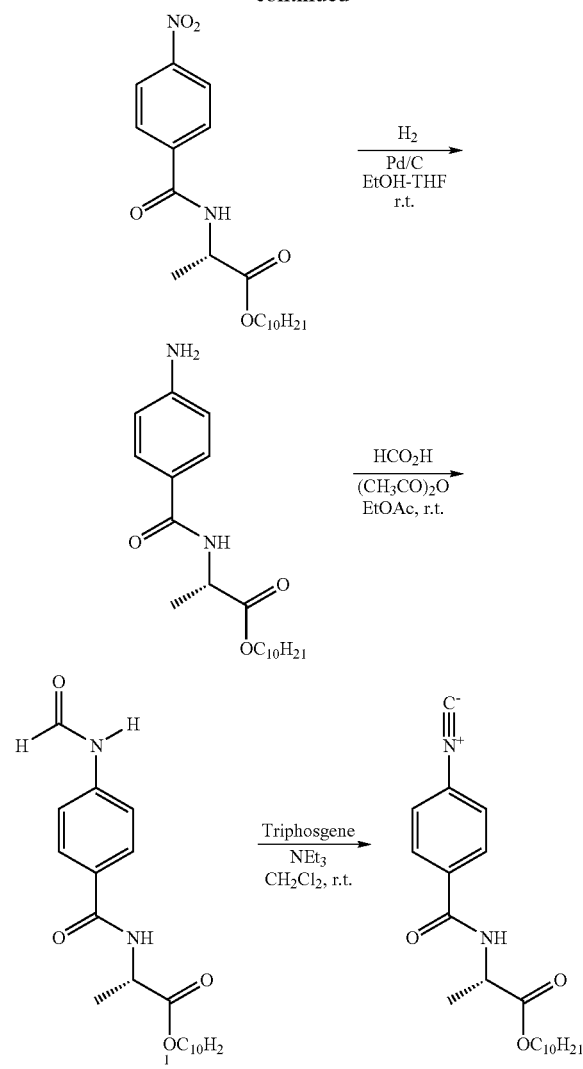

Nitrobenzoic acid was reacted with L-alanine decyl ester in t-butanol and dimethyl acetamide (DMA) in the presence of DCC as a coupling agent for amidation. Thus-obtained amide compound was reduced by a conventional reducing method so that the nitro group is reduced to an amino group. Then, it was reacted with formic acid in ethyl acetate in the presence of anhydrous acetic acid for N-formylation to give 4-formaminobenzoyl-L-alanine decyl ester.

4-Formaminobenzoyl-L-alanine decyl ester (200 mg, 0.531 mmol) obtained above was added to a dried three-neck flask (100 mL), fully de-aerated, purged with argon gas, and then dry dichloromethane (6 mL) and triethylamine (0.148 mL, 1.06 mmol) were added thereto and dissolved with stirring on an ice bath. After that, triphosgene (87 mg, 0.292 mmol) which had been dissolved in dry dichloromethane (10 mL) was added thereto and the mixture was stirred at room temperature for one hour. After completion of the reaction, to the reaction solution to which 50 mL of dichloromethane had been further added a saturated aqueous solution of sodium hydrogen carbonate (100 mL) was added, extracted, and then dehydrated with anhydrous magnesium sulfate (20 mg). After removing dichloromethane under reduced pressure, a desired isocyanide product was isolated by silica gel column chromatography.

Example 2

Preparation of poly(4-isocyanobenzoyl-L-alanine Decyl Ester) which has a Right-Handed Helical Structure Shown Below: Preparation of Polymer L1R

[Chemical Formula 9]

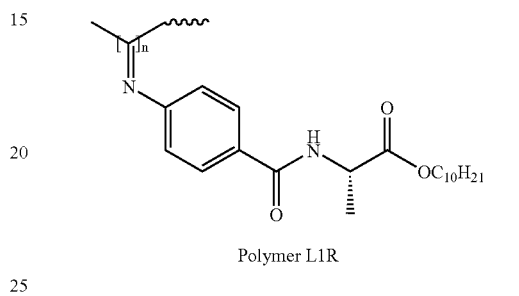

Polymer L1R

In a dried polymerization tube (10 mL), 4-isocyanobenzoyl-L-alanine decyl ester (50 mg, 0.140 mmol) as a starting monomer was placed, and the tube was fully de-aerated, purged with nitrogen, and then carbon tetrachloride (1.4 mL) was added thereto and dissolved by stirring at room temperature. Then, a solution of nickel chloride hexahydrate (0.33 mg) which had been dissolved in dry ethanol (14 μL) was added thereto, and the reaction liquid was stirred for 24 hours at room temperature under the nitrogen atmosphere. After completion of the reaction, the reaction liquid was added dropwise to methanol and separated by centrifugation with speed of 3000 revolution/min. Thus-obtained precipitate was collected and dried to give poly(4-isocyanobenzoyl-L-alanine decyl ester) (herein after, referred to as polymer L1R). The number average molecular weight of the resulting polymer was approximately 84,000.

Example 3

Preparation of poly(4-isocyanobenzoyl-L-alanine Decyl Ester) which has a Left-Handed Helical Structure Shown Below: Preparation of Polymer L1L

[Chemical Formula 10]

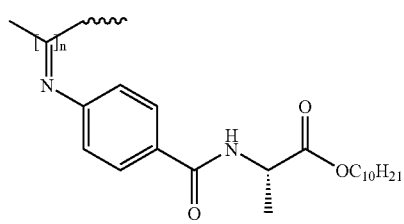

Polymer L1L

In a dried polymerization tube (10 mL), 4-isocyanobenzoyl-L-alanine decyl ester (50 mg, 0.140 mmol) as a starting monomer was placed, and the tube was fully de-aerated, purged with nitrogen, and then toluene (1.4 mL) was added thereto and dissolved by stirring at room temperature. Then, a solution of nickel chloride hexahydrate (0.33 mg) which had been dissolved in dry ethanol (14 µL) was added thereto, and the reaction liquid was stirred for six days at 100° C. under the nitrogen atmosphere. After completion of the reaction, the reaction liquid was added dropwise to methanol and separated by centrifugation with speed of 3000 revolution/min. Thus-obtained precipitate was collected and dried to give poly(4-isocyanobenzoyl-L-alanine decyl ester) (hereinafter, referred to as polymer L1L). The number average molecular weight of the resulting polymer was approximately 230,000.

Example 4

Identification of the Handedness of Main Chain Helical Structure of poly(4-isocyanobenzoyl-L-alanine Decyl Ester) Polymer L1R and Polymer L1L which have Either a Right-Handed Helical Structure or a Left-Handed Helical Structure as Prepared in Example 2 and 3 Above by Measuring the CD Spectrum of the Polymer 1 mg each of polymer L1R and polymer L1L were dissolved in 5 mL chloroform, respectively. Ellipsoidal spectrum (CD) was then measured therefor. As a result, for polymer L1R a positive CD peak originating from the polymer main chain was observed in the wavelengths of 320 to 400 nm, while for polymer L1L a negative CD peak originating from the polymer main chain was observed in the wavelengths of 320 to 400 nm. The results are illustrated in FIG. 1, in which the solid line represents the polymer L1R and the broken line represents the polymer L1L.

Taken together the above results showing that the polymer L1R gives a positive CD peak in the region of 300 to 400 nm and the polymer L1L gives a negative CD peak in the same region, it was found that polymer L1R has a right-handed main chain helical structure while polymer L1L has a left-handed main chain helical structure.

Further, the handedness of main chain helical structure of poly(4-isocyanobenzoyl-L-alanine decyl ester) polymer L1R and polymer L1L which have either a right-handed helical structure or a left-handed helical structure was determined by AFM measurement.

Polymer L1R and polymer L1L (0.2 mg each) were dissolved in toluene (1 mL), respectively. The resulting solution was spin-cast on HOPG (highly oriented pyrolytic graphite), and then the surface was observed by using AFM (atomic force microscope). The results are given in FIG. 2 and FIG. 3, for the polymer L1R and the polymer L1L, respectively.

As a result of the observation, it was evident that the polymer L1R has a right-handed helical structure (FIG. 2) and the polymer L1L has a left-handed helical structure (FIG. 3). The left column in FIG. 2 and the right column in FIG. 3 are the model structures that are established based on the observation results.

Comparative Example 1

Preparation of Lactic Acid Decyl Ester Derivative which does not have an Amide Group as a Substituent With the same method described in the above Examples, poly(4-isocyanobenzoyl-L-lactic acid decyl ester) lacking an amide bond as a substituent was prepared according to the following reaction scheme.

[Chemical Formula 11]

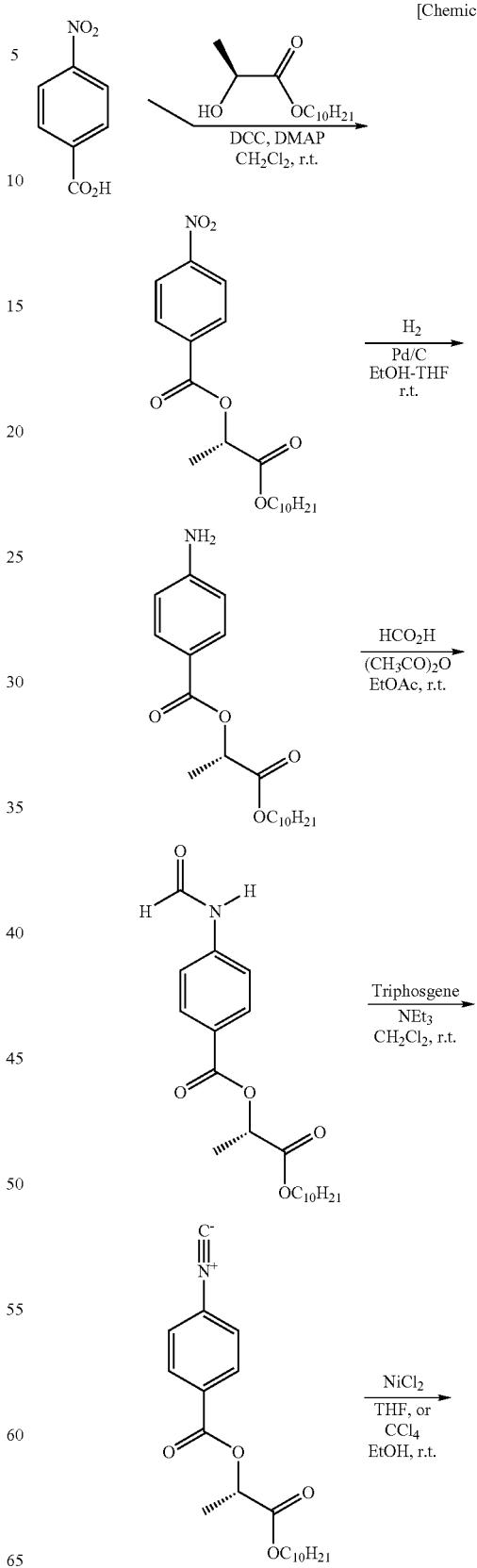

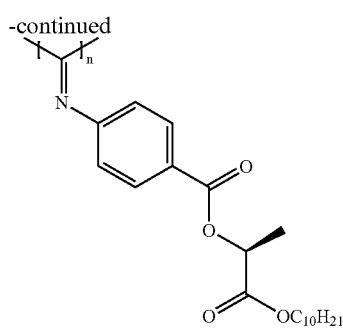

(1) Synthesis of 4-isocyanobenzoyl-L-lactic Acid Decyl Ester as a Starting Monomer In a three-neck flask (100 mL), 4-formaminobenzoyl-L-lactic acid decyl ester (200 mg, 0.530 mmol) was placed, and the flask was fully de-aerated, purged with argon gas, and then dry dichloromethane (6 mL) and triethylamine (0.148 mL, 1.06 mmol) were added thereto and dissolved with stirring on an ice bath. After that, triphosgene mg, 0.292 mmol) which had been dissolved in dry dichloromethane (10 mL) were added thereto and stirred at room temperature for one hour. After completion of the reaction, to the reaction solution to which 50 mL of dichloromethane had been further added a saturated aqueous solution of sodium hydrogen carbonate (100 mL) was added, extracted, and then dehydrated with anhydrous magnesium sulfate (20 mg).

After removing dichloromethane under reduced pressure, a desired product was isolated by silica gel column chromatography.

(2) Synthesis of poly(4-isocyanobenzoyl-L-lactic Acid Decyl Ester): Polymer L2R Shown Below

[Chemical Formula 12]

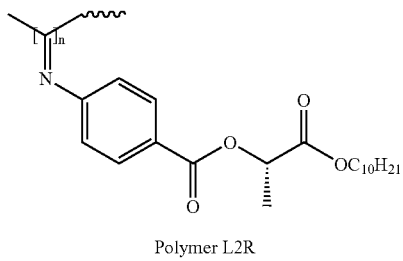

Polymer L2R

In a dried polymerization tube (10 mL), 4-isocyanobenzoyl-L-lactic acid decyl ester (50 mg, 0.140 mmol) as a starting monomer was placed, and the tube was fully de-aerated, purged with nitrogen, and then carbon tetrachloride (1.4 mL) was added thereto and dissolved by stirring at room temperature. Then, a solution of nickel chloride hexahydrate (0.33 mg) which had been dissolved in dry ethanol (14 μL) was added thereto, and the reaction liquid was stirred for 24 hours at room temperature under the nitrogen atmosphere. After completion of the reaction, the reaction liquid was added dropwise to methanol and separated by centrifugation with speed of 3000 revolution/min. Thus-obtained precipitate was collected and dried to give poly(4-isocyanobenzoyl-L-lactic acid decyl ester) (herein after, referred to as polymer L2R).

The number average molecular weight of the resulting polymer was approximately 270,000.

(3) Synthesis of poly(4-isocyanobenzoyl-L-lactic Acid Decyl Ester): Polymer L2L Shown Below

[Chemical Formula 13]

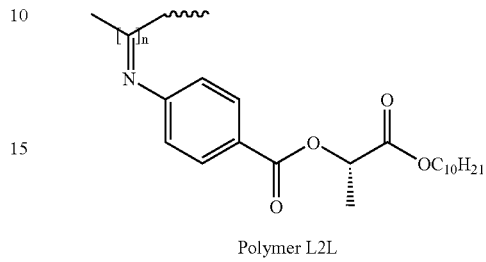

Polymer L2L

In a dried polymerization tube (10 mL), 4-isocyanobenzoyl-L-lactic acid decyl ester (50 mg, 0.140 mmol) as a starting monomer was placed, and the tube was fully de-aerated, purged with nitrogen, and then toluene (1.4 mL) was added thereto and dissolved by stirring at room temperature. Then, a solution of nickel chloride hexahydrate (0.33 mg) which had been dissolved in dry ethanol (14 μL) was added thereto, and the reaction liquid was stirred for six days at 100° C. under the nitrogen atmosphere. After completion of the reaction, the reaction liquid was added dropwise to methanol and separated by centrifugation with speed of 3000 revolution/min. Thus-obtained precipitate was collected and dried to give poly(4-isocyanobenzoyl-L-lactic acid decyl ester) (herein after, referred to as polymer L2L). The number average molecular weight of the resulting polymer was approximately 220,000.

(4) Identification of the Handedness of Main Chain Helical Structure of poly(4-isocyanobenzoyl-L-lactic Acid Decyl Ester) Polymer L2R and Polymer L2L by Measuring the CD Spectrum of the Polymer 1 mg each of the polymer L2R and the polymer L2L were dissolved in 5 mL chloroform, respectively. Ellipsoidal spectrum (CD) was then measured therefor. As a result, for both of the polymer L2R and the polymer L2L a negative CD peak originating from the polymer main chain was observed in the wavelengths of 320 to 400 nm. The results are illustrated in FIG. 4, in which the solid line represents the polymer L2R and the broken line represents the polymer L2L.

Taken together the above results showing that the polymer L2R and the polymer L2L both lacking an amide bond as a substituent give a negative CD peak in the region of 300 to 400 nm, it is found that both of the polymer L2R and the polymer L2L have a left-handed main chain helical structure. Consequently, it is evident that a polymeric material having controlled helical structure cannot be obtained from an isocyanide monomer which lacks an amide bond as a substituent.

Preparation Example 1

Preparation of 4-isocyanobenzoyl-L-alanine Decyl Ester Monomer

According to the method by Kajitani, et. al. (T. Kajitani, K. Okoshi, S.-i. Sakurai, J. Kumaki, E. Yashima, J. Am. Chem.

Soc. 2006, 128, 708-709), 4-isocyanobenzoyl-L-alanine decyl ester was prepared by following the reaction scheme shown below.

[Chemical Formula 14]

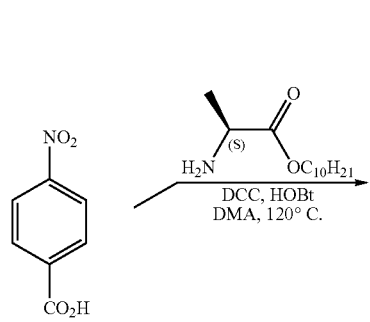

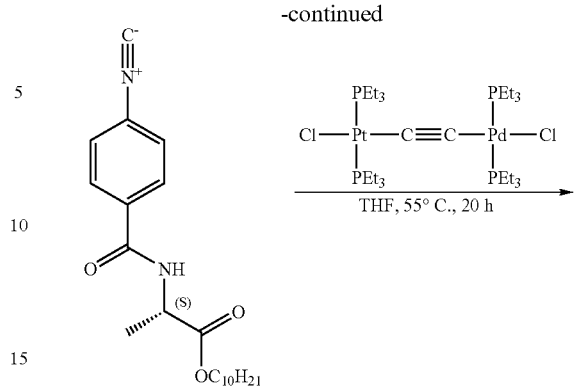

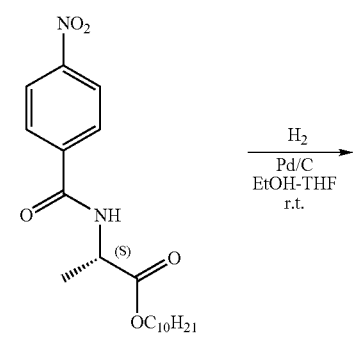

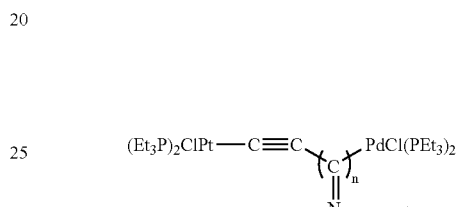

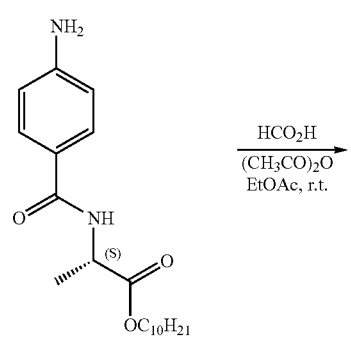

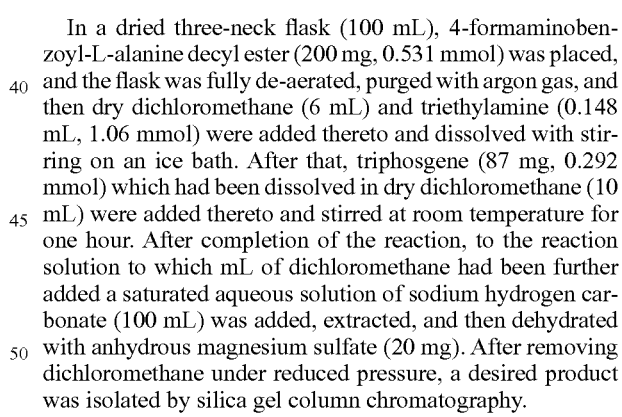

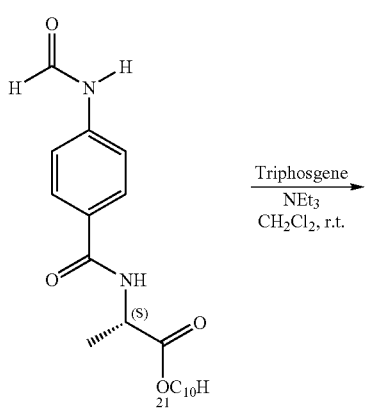

In a dried three-neck flask (100 mL), 4-formaminobenzoyl-L-alanine decyl ester (200 mg, 0.531 mmol) was placed, and the flask was fully de-aerated, purged with argon gas, and then dry dichloromethane (6 mL) and triethylamine (0.148 mL, 1.06 mmol) were added thereto and dissolved with stirring on an ice bath. After that, triphosgene (87 mg, 0.292 mmol) which had been dissolved in dry dichloromethane (10 mL) were added thereto and stirred at room temperature for one hour. After completion of the reaction, to the reaction solution to which mL of dichloromethane had been further added a saturated aqueous solution of sodium hydrogen carbonate (100 mL) was added, extracted, and then dehydrated with anhydrous magnesium sulfate (20 mg). After removing dichloromethane under reduced pressure, a desired product was isolated by silica gel column chromatography.

Preparation Example 2

Preparation of Binuclear platinum-palladium-m-ethynediyl Complex that is Crosslinked with Acetylene Binuclear platinum-palladium-m-ethynediyl complex that is crosslinked with acetylene and has a characteristic of living polymerization for isocyanide was prepared according to the method by Onitsuka, et. al. (K. Onitsuka, K. Yanai, F. Takei, T. Joh, S. Takahashi, Organometallics 1994, 13, 3862-3867. K. Onitsuka, T. Joh, S. Takahashi, Bull. Chem. Soc. Jpn. 1992, 65, 1179-1181).

Example 5

Preparation of a Mixture of poly(4-isocyanobenzoyl-L-alanine decyl ester) which has a Right-Handed Helical Structure or a Left-Handed Helical Structure Shown Below

[Chemical Formula 15]

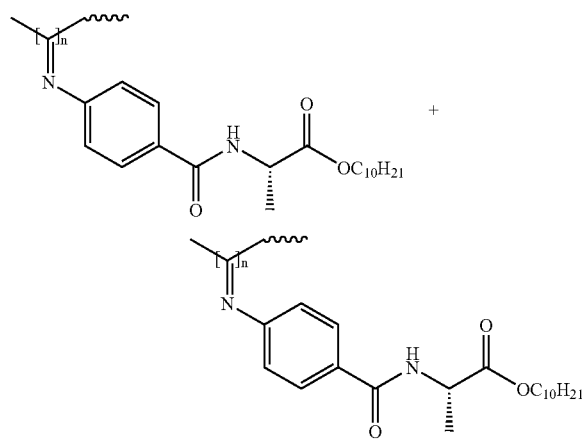

In a dried polymerization tube (20 mL), 4-isocyanobenzoyl-L-alanine decyl ester as a starting monomer which had been prepared in the above Preparation example 1 was placed, and dried under reduced pressure. A 3-way cock was attached to the tube and 1.35 mL of tetrahydrofuran (THF) which had been previously fully dried was added thereto via syringe. Then, THF solution comprising binuclear platinum-palladium-m-ethynediyl complex (5.6 mM, 0.5 mL) which is crosslinked with acetylene and has a characteristic of living polymerization for isocyanide, as prepared separately before, was added to the tube via syringe. In this case, the concentration of the starting monomer and the catalyst for polymerization was 0.2 M and 0.002 M, respectively. The reaction solution was stirred at 55° C. for twenty hours under the nitrogen atmosphere. Thus-obtained polymer was re-precipitated in a large amount of methanol, collected by centrifugation and dried under reduced pressure at room temperature. The desired polymer ((±) form) was obtained in an amount of 100 mg (Yield; 100%). Spectral data of the obtained polymer ((±) form) is given below.

IR (CHCl$_3$, cm$^{-1}$): 3284 ($\nu_{N-H}$), 1744 ($\nu_{C=O}$ Ester), 1633 (Amide I), 1534 (Amide II);
$^1$H NMR (CDCl$_3$, 55° C.): δ
0.87 (broad, CH3, 3H), 1.26 (broad, CH2, 14H),
1.53 (broad, CH3 and CH2, 5H), 4.09 (broad, CH2, 2H),
4.51 (broad, CH, 1H), 4.8-7.7 (broad, aromatic, 4H),
7.9-9.0 (broad, NH, 1H);
$[\alpha]_D^{25}$ −995° (c 0.1, chloroform);
As elemental analysis (C$_{21}$H$_{30}$N$_2$O$_3$)n:
Calculated value C, 70.36; H, 8.44; N, 7.81.
Observed value C, 70.23; H, 8.56; N, 7.68.

Example 6

Separation of a Mixture of poly(4-isocyanobenzoyl-L-alanine decyl ester) Having Both of a Right-Handed Helical Structure and a Left-Handed Helical Structure into the Isomers Having Single-Handedness, i.e., Isomer Exclusively Having a Right-Handed Helical Structure and the Other Isomer Exclusively Having a Left-Handed Helical Structure The polymer (70.8 mg) which had been obtained in the above Example 5 was suspended in acetone (30 mL), and stirred at room temperature for three hours. After the filtering, the filtrate liquid was dried to obtain (+) form (10.0 mg, 14%).

In addition, the polymer which had been obtained as an insoluble matter in acetone was dissolved in a small amount of chloroform, re-precipitated in a large amount of acetone, and filtered. After repeating several times these steps, (−) form was obtained (44.5 mg, 63%). Thus-obtained (+) form and (−) form had a spectral data as follows.

(+) Form:
IR (CHCl$_3$, cm$^{-1}$): 3270 ($\nu_{N-H}$), 1742 ($\nu_{C=O}$ Ester), 1636 (Amide I), 1532 (Amide II);
$^1$H NMR (CDCl$_3$, 55° C.): δ
0.90 (broad, CH3, 3H), 1.29 (broad, CH2, 14H),
1.62 (broad, CH3 and CH2, 5H), 4.11 (broad, CH2, 2H),
4.51 (broad, CH, 1H), 4.9-7.7 (broad, aromatic, 4H),
8.3-9.0 (broad, NH, 1H);
$[\alpha]_D^{25}$ +1530° (c 0.05, chloroform);
As elemental analysis (C$_{21}$H$_{30}$N$_2$O$_3$)n:
Calculated value C, 70.36; H, 8.44; N, 7.81.
Observed value C, 70.18; H, 8.44; N, 7.78.

(−) Form:
IR (CHCl$_3$, cm$^{-1}$): 3284 ($\nu_{N-H}$), 1743 (($\nu_{C=O}$ Ester), 1633 (Amide I), 1534 (Amide II).
$^1$H NMR (CDCl$_3$, 55° C.): δ
0.87 (broad, CH3, 3H), 1.25 (broad, CH2, 14H),
1.53 (broad, CH3 and CH2, 5H), 4.09 (broad, CH2, 2H),
4.51 (broad, CH, 1H), 4.8-7.7 (broad, aromatic, 4H),
7.9-8.9 (broad, NH, 1H);
$[\alpha]_D^{25}$ −1615° (c 0.1, chloroform);
As elemental analysis (C$_{21}$H$_{30}$N$_2$O$_3$)n:
Calculated value C, 70.36; H, 8.44; N, 7.81.
Observed value C, 70.35; H, 8.36; N, 7.64.

Example 7

Identification of the Handedness of Main Chain Helical Structure of (−) Form and (+) Form of poly (4-isocyanobenzoyl-L-alanine Decyl Ester) which have Either a Right-Handed Helical Structure or a Left-Handed Helical Structure by Measuring the CD Spectrum of the Polymer For each polymer described above, the results obtained from SEC measurement and CD spectral measurement in chloroform are given in FIG. 5 and FIG. 6, respectively. Furthermore, molecular weight data and circular dichroism from CD spectrum were obtained for (±) form, (−) form and (+) form and each results are summarized in the following Table 1.

TABLE 1

| polymer | Molecular weight | | | Ellipticity (CD) |
| --- | --- | --- | --- | --- |
| | $M_n$ | $M_w$ | $M_w/M_n$ | $\Delta_{\epsilon 364}$ ($M^{-1}$ $cm^{-1}$) |
| (±) form | $9.5 \times 10^4$ | $1.1 \times 10^5$ | 1.16 | −11.8 |
| (+) form | $5.6 \times 10^4$ | $6.2 \times 10^4$ | 1.11 | +20.3 |
| (−) form | $1.2 \times 10^5$ | $1.3 \times 10^5$ | 1.06 | −20.7 |

SEC measurement was carried out for (±) form which had been obtained as an insoluble matter in methanol. As a result, it was shown that the produced polymer has bimodality, indicating that it exists as a mixture of two components having a different molecular weight (see, FIG. 5). Each polymer showed a CD spectrum with different sign. In this connection, a solvolytic resolution was carried out using acetone to obtain the polymers (insoluble matter: (−) form, soluble matter: (+) form), and then SEC measurement was carried out again. As a result, it was found that each polymer had a chromatogram with a monomodal peak, and number weight molecular weight (Mn) and polydispersity (Mw/Mn) were 120,000 and 1.06 for (−) form and 56,000 and 1.11 for (+) form, respectively (see, FIG. 5 and Table 1). From these results, it was confirmed that the (±) form, which had been obtained as a methanol insoluble matter, is a mixture of two components having different handedness of its main chain helical structure and different molecular weight, and the polymers consisting of such different components have different solubility in acetone.

Next, circular dichroism (CD) spectrum of the (±) form before the separation was measured in chloroform. As a result, a negative Cotton effect was observed near 360 nm which is a main absorption region of the main chain of the polymer (see, FIG. 6). This result suggests that the (±) form forms a helical structure of which handedness is predominantly one of right- and left-handedness. Moreover, CD spectrum of (−) form and (+) form showed Cotton effect that is opposite to each other, their pattern was close to an enantiomeric relationship and the CD spectral strength was very strong compared to that of the (±) form before the separation. FIG. 6 shows CD spectrum at room temperature for each of the polymers.

Taken together, these results suggest that the (−) form and the (+) form of the present invention have helical structures with opposite handedness in a diastereomeric relationship. In addition, it indicates that both helical polymers are produced as a living polymer during the polymerization reaction.

It has been known from a Non-Patent Document that the handedness of a helical structure of helical polyisocyanide polymer species is as follows: a positive peak appearing near 300 to 400 nm in CD spectrum, which is a main absorption band, indicates right-handedness of the main chain helix, while a negative peak appearing near the region indicates left-handedness of the main chain helix (see, Takei, F.; Hayashi, H.; Onitsuka, K.; Kobayashi, N.; Takahashi, S. Angew. Chem., Int. Ed. 2001, 40, 4092-4094).

From FIG. 6 wherein the (+) form shows a positive peak near 300 to 400 nm in CD spectrum while the (−) form shows a negative peak near the same region, it was confirmed that the (+) form has a right-handed main chain helical structure and the (−) form has a left-handed main chain helical structure.

Example 8

Identification of the Handedness of Main Chain Helical Structure of (−) Form and (+) Form of poly (4-isocyanobenzoyl-L-alanine Decyl Ester) which have Either a Right-Handed Helical Structure or a Left-Handed Helical Structure by AFM Next, the helical structures of the (−) form and the (+) form were directly observed by AFM. Thus-obtained results are given in FIG. 7. As a result, for the (−) form showing the negative Cotton effect for the main chain region of the polymer left-handed helical structure was observed, and for the (+) form showing the positive Cotton effect for the main chain region of the polymer right-handed helical structure was observed. After additionally carrying out AFM observation in a broader range, it was found that each helical structure is almost exclusively single-handed. That is, the (−) form and the (+) form respectively have a right-handed or left-handed helical structure that are in a diastereomeric relationship.

Example 9

Identification of Smectic Phase of Concentrated Chloroform Solution of the (−) Form and (+) Form of poly(4-isocyanobenzoyl-L-alanine Decyl Ester) which have Either a Right-Handed Helical Structure or a Left-Handed Helical Structure Based on Polarizing Microscopic Photograph For each of the polymers, a concentrated chloroform solution was prepared (approximately 15%), and polarizing microscopic measurement was carried out therefor. Results are given in FIG. 8. For both of the (−) form and (+) form, a fan-shaped texture, that is characteristic for a smectic liquid crystal phase, was observed. From this result, it was confirmed that both of the (−) form and (+) form form a smectic phase in a concentrated chloroform solution.

Example 10

AFM Observation of the Higher Structure in the Cast Film Comprising (−) Form and (+) Form of poly(4-isocyanobenzoyl-L-alanine Decyl Ester) which have Either a Right-Handed Helical Structure or a Left-Handed Helical Structure For each of the polymer, AFM observation of the film in which the polymer had been cast was carried out. Results are given in FIG. 9. Consequently, a clear lamellar structure was observed for both of the (−) form and the (+) form, indicating that they all form a smectic phase.

Example 11

Small-Angle X Ray Scattering Experiment on the Cast Film Comprising (−) Form and (+) Form of poly(4-isocyanobenzoyl-L-alanine decyl ester) which have Either a Right-Handed Helical Structure or a Left-Handed Helical Structure For each of the polymer, small-angle X ray scattering experiment was carried out with a solid sample which had been prepared by slow evaporation of the solvent from the chloroform concentrated solution. As a result, small-angle reflection appeared at the scattering angle (2θ) of 0.92° and 1.51° for the (−) form and the (+) form, respectively. Their plane gap was 95.6 Å (angstrom) and 58.4 Å (angstrom), respectively. Results are given in FIG. 10. Considering that these values are almost the same as the length of the molecule determined from AFM measurement, it was found that both of the (−) form and the (+) form form a smectic phase.

INDUSTRIAL APPLICABILITY

Simple and low-cost production of a polymeric material having a right-handed or left-handed helix structure from a single type monomer is very important to improve resolution efficiency in its use as a filler for optical resolution column chromatography, a catalyst for asymmetric synthesis, and an optically active ligand material, etc. and also to obtain an optically active compound desired in an asymmetric synthesis.

Thus, the present invention is to provide a simple and low-cost method for the production of a polymeric material having a right-handed or left-handed helix structure from a single type monomer, and a monomer that can be used therefor. In this connection, the present invention will be very useful not only for a material industry but also for a chemical industry which uses such material as a filler for optical resolution column chromatography, a catalyst for asymmetric synthesis, and an optically active ligand material, etc., a liquid crystal industry, and an optical material or an optical element industry.

The invention claimed is:

1. A polyaromatic isocyanide derivative having a helical main chain structure represented by the following general formula (1):

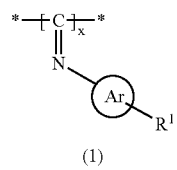

[Chemical Formula 1]

(1)

wherein, Ar represents a benzene ring of 6 to 30 carbon atoms, $R^1$ represents an aminocarbonyl group of an optically active alanine ester that is esterified with an alkyl group of 6 to 30 carbon atoms, the optically active alanine is any of levorotatory (S) or dextrorotatory (R) chiral body, and x is a positive number indicating the repeat of polyisocyanide group.

2. A polyaromatic isocyanide derivative according to claim 1 wherein the polyaromatic isocyanide derivative is a polyaromatic isocyanide derivative which can form a hydrogen bond between the adjacent amide groups on a side chain.

3. A polyaromatic isocyanide derivative according to claim 1 wherein the polyaromatic isocyanide derivative has a persistence length of 100 nm or more.

4. A liquid crystalline composition comprising a polyaromatic isocyanide derivative of claim 1.

* * * * *